(12) United States Patent
Hajianpour

(10) Patent No.: US 6,197,027 B1
(45) Date of Patent: Mar. 6, 2001

(54) DEVICE FOR EXTERNAL FIXATION OF A FRACTURED RADIUS

(76) Inventor: Mohammed Ali Hajianpour, 1706 Vestal Dr., Coral Springs, FL (US) 33071

( * ) Notice: Subject to any disclaimer, the term of this patent is extended or adjusted under 35 U.S.C. 154(b) by 0 days.

(21) Appl. No.: 09/391,164

(22) Filed: Sep. 8, 1999

(51) Int. Cl.[7] .................................................. A61B 17/60
(52) U.S. Cl. .............................................. 606/59; 606/57
(58) Field of Search .................................. 606/54, 55, 56, 606/57, 58, 59, 60, 61, 67, 69, 70, 71, 72, 73

(56) References Cited

U.S. PATENT DOCUMENTS

| | | | |
|---|---|---|---|
| 4,554,915 | 11/1985 | Brumfield | 128/92 A |
| 4,662,365 | * 5/1987 | Gotzen et al. | 606/59 |
| 4,714,076 | 12/1987 | Comte et al. | 128/92 ZW |
| 4,747,400 | 5/1988 | Koeneman et al. | 128/92 Z |
| 4,867,144 | * 9/1989 | Karas et al. | 606/54 |
| 5,006,120 | 4/1991 | Carter | 606/69 |
| 5,015,248 | * 5/1991 | Burstein et al. | 606/69 |
| 5,197,966 | * 3/1993 | Sommerkamp | 606/69 |
| 5,545,162 | 8/1996 | Huebner | 606/57 |
| 5,586,985 | * 12/1996 | Putnam et al. | 606/69 |
| 5,741,251 | 4/1998 | Benoist | 606/54 |
| 5,749,872 | * 5/1998 | Kyle et al. | 606/69 |

* cited by examiner

Primary Examiner—Pedro Philogene
(74) Attorney, Agent, or Firm—Ronald V. Davidge

(57) ABSTRACT

A fixture for external bone fixation includes a number of pins clamped within pin mounting holes. Each pin extends through a flexible sleeve and through a clamping nut. Each pin mounting hole includes a pilot hole guiding the pin and an internally threaded portion engaging an externally threaded portion of the clamping nut. As the clamping nut is tightened, the flexible sleeve is longitudinally compressed, so that it expands transversely to clamp itself within the pin mounting hole and to clamp the pin within itself. A fixture configured particularly for external fixation of a fractured distal radius includes a number of such pins configured for attachment within a shaft portion of the radius and a number of such pins configured to attachment to a fragment of the fractured radius. The fixture also includes a sliding attachment block supporting a number of pins extending for lateral attachment to such a fragment.

20 Claims, 1 Drawing Sheet

US 6,197,027 B1

DEVICE FOR EXTERNAL FIXATION OF A FRACTURED RADIUS

BACKGROUND OF THE INVENTION

1. Field of the Invention

This invention relates to clamping pins within devices for external fixation of fractured bones, and, more particularly, to an external fixture in which pins are clamped for fixation of a fractured radius.

2. Background Information

The fracture of the distal radius is one of the most common human fractures, occurring in as many as 350,000 people per year in the United States alone. The conventional processes both for reducing such a fracture and for maintaining the bones in proper alignment during the subsequent healing process involves applying and maintaining an extension force across the fracture, with ligamental taxis being relied upon to hold the bones in place. The process for treating a fractured distal radius is described in the 1901 edition of *Gray's Anatomy* in the following manner, "The treatment consists of flexing the forearm, and making a powerful extension from the wrist and elbow, depressing at the same time the radial side of the hand, and retaining the parts in that position by well-padded pistol-shaped splints."

A common method for the treatment of a fractured distal radius involves the use of standard immobilizing cast techniques, preventing movement of the radiocarpal joint throughout the course of rehabilitation. A problem with this method is that it sometimes results in inadequate internal fixation, which can cause deformity, pain, and prolonged disability.

The process of external pin fixation is often used in the repair of a fractured distal radius. This process initially involves the surgical insertion of skeletal traction pins on both sides of the fracture, with a frame being connected to the pins for immobilizing the bones, and for holding them together until the fracture is mended. Conventional methods for applying external pin fixation for the treatment of a fractured distal radius provide for the immobilization of the radiocarpal joint, so that the hand cannot be flexed. Examples of frames used in this way are found in U.S. Pat. Nos. 4,554,915 and 5,545,162. Each of these frames rigidly but adjustably connects a pair of pins extending into the metacarpal bones with a pair of pins extending into the radius on the proximal side of the fracture. While this type of fixation often provides an improvement over conventional casting techniques in the management of severe fractures of the distal radius, immobilization of the radiocarpal joint during the treatment period typically results in a long period of stiffness and disability after the external fixation device is removed. Typically the external fixation device is left in place during the healing process for six to eight weeks. After the fixation device is removed, three to six months are required for the patient to regain motion of his hand. Thus, what is needed is a fixation device providing adequate fixation during the healing process while allowing flexure in the radiocarpal joint.

A fractured distal radius may alternately be repaired using a permanently installed fixation plate with screws and blades extending into the radius and into the broken-away fragment, as described, for example, in U.S. Pat. No. 5,006, 120. What is needed is a method for combining the benefit of this method for installing an internal fixation plate, in terms of early flexure of the hand at the radiocarpal joint, with the benefit of the relatively simple surgical procedures of external pin fixation.

U.S. Pat. No. 4,747,400 describes an external fixation frame including a proximal carriage on one end and a distal carriage on the other end. The proximal carriage is adapted to mount pins inserted into the proximal bone segment, and is supported on the frame by support arms which are movable with respect to the frame. The distal carriage includes a clamping member, adapted to mount pins inserted in the distal bone segment, which is pivotal about the fracture to permit precise alignment of the distal and proximal bone segments. A fragment support, mounted to one of the side rails of the support arm for the proximal carriage, is adapted to clamp a pin inserted within a central fragment positioned between the proximal and distal segments of a comminuted fracture.

The external fixation frame of U.S. Pat. No. 4,747,400 is a general purpose device for dealing with fractures of long bones, such as the femur, tibia, humerus, ulna, and tibia, as well as the radius. Since fractures of the distal radius are particularly common, what is needed is an external fixation device configured particularly for the treatment of such fractures, without the bulk, weight, and complexity of a general purpose device.

SUMMARY OF THE INVENTION

According to one aspect of the present invention, there is provided apparatus for clamping an external fixation pin within a fixation device. The pin extends inwardly from the fixation device for attachment within bone and outwardly for attachment to a rotary driving device. The apparatus includes a pilot hole and an internally threaded hole within the fixation device, along with a flexible sleeve and a clamping nut. The pin extends through the pilot hole and through holes within the flexible sleeve and the clamping nut. The clamping nut includes an externally threaded section engaging the internally threaded hole. Turning the clamping nut to move the clamping nut inward compresses the flexible sleeve in a direction parallel to a longitudinal axis of the flexible sleeve, so that the flexible sleeve expands transversely to clamp around the pin and to clamp within the internally threaded hole.

According to another aspect of the present invention, there is provided apparatus for the external fixation of a fractured distal radius. The apparatus includes a plate, first and second pluralities of pin mounting holes, and first and second pluralities of pins. The first plurality of pin mounting holes extend in a line within the plate for securing pins in the shaft portion of the radius. The second plurality of pin mounting holes extend in a two-dimensional array for securing pins in a fragment of the fractured distal radius. The first plurality of pins individually extend within various of the pin mounting holes within the first plurality of pin mounting holes, while the second plurality of pins individually extend within various of the pin mounting holes within the second plurality of pin mounting holes. Each pin extends in a first direction from the plate for attachment within bone.

DETAILED DESCRIPTION OF THE INVENTION

Figure 1:
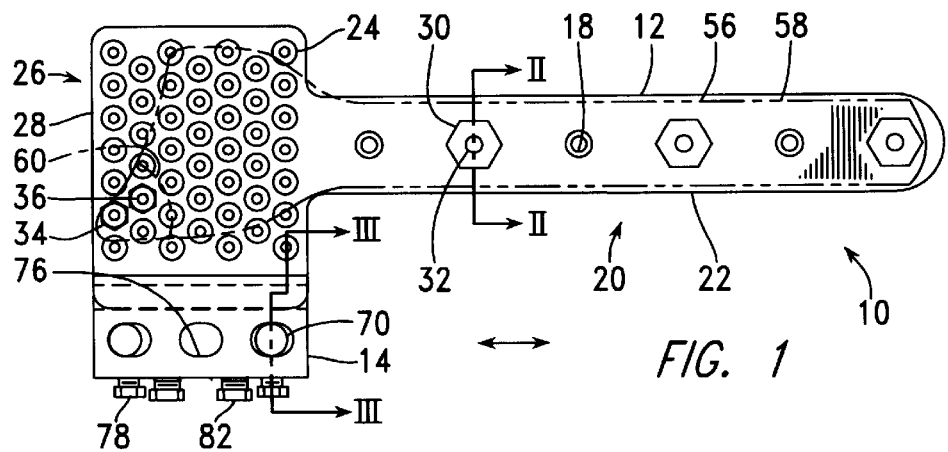
FIG. 1 is a plan view of a fixation device, for external pin fixation, built in accordance with the present invention.

FIG. 1 is a plan view of a fixation device, generally indicated as 10, built in accordance with the present invention, being particularly configured for treatment of a fractured distal radius of the right arm. This fixation device includes a plate 12 and a attachment block 14, mounted to slide on the plate 12 in the longitudinal directions indicated by arrow 16. The plate 12 includes a number of pin mounting holes 18, extending in a first pin mounting pattern 20 along a line within a elongated section 22 of the plate 12. The plate 12 also includes a number of pin mounting holes 24, extending within a second pin mounting pattern 26 in an array within a widened section 28 of the plate 12. Each of the pin mounting holes 18 defines a location at which a first type of pin clamping mechanism 30 may be placed to hold a pin 32 in place. Similarly, each of the pin mounting holes 24 defines a location at which a second type of pin clamping mechanism 34 may be placed to hold a pin 36 in place. In general, only some of the pin mounting holes 18, 24 are used at a time, with the remaining pin mounting holes 18,24 being empty. Relatively large numbers of holes 18, 24 are provided within the pin mounting patterns 20, 26 to accommodate differences among individual radius bones and among individual fracture patterns.

Figure 2:
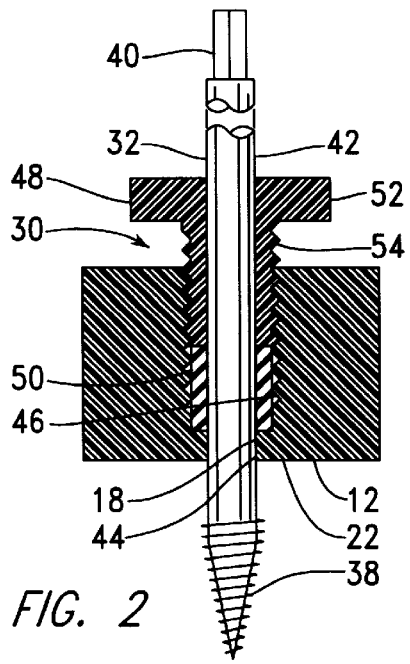
FIG. 2 is a first transverse cross-sectional view, taken as indicated by section lines II—II in FIG. 1 to show a first pin clamping mechanism in the fixation device of FIG. 1.

FIG. 2 is a transverse cross-sectional view of the elongated section 22 of plate 12, taken in the direction indicated by section lines II—II in FIG. 1 to show the components of a pin mounting hole 18 and of the first type of pin clamping mechanism 30. The pin 32 being clamped by this mechanism 30 includes a threaded portion 38 for forming a hole in bone with rotation of the pin 32, a hexagonally-shaped upper portion 40 for attachment to an electrical or pneumatically-driven drill, and a smooth shank 42 along which attachment is made to the plate 12. The pin mounting hole 18 includes a pilot hole 44 for locating the pin 32 and an internally threaded portion 46. The pin clamping mechanism 30 includes a pin clamping nut 48 and a flexible sleeve 50. The pin clamping nut 48 has a hexagonally-shaped head 52 and an externally-threaded section 54.

Referring to FIGS. 1 and 2, the fixation device 10 is fastened in place above the arm (not shown), which is oriented so that the palm of the hand faces downward. The general shape of the radius, underlying the plate 12 within the arm, is indicated by a phantom line 56. The fixation device 10 is first fastened to the shaft 58 of the radius 56 with two or more pins 32 being driven into the bone by rotation of a driving device (not shown) engaging the hexagonally-shaped coupling portions 40 of the pins 32. The pins 32 are held in alignment with the fixation device 10 by means of the pilot holes 44 through which they extend. After a pin 32 is driven into the bone as far as necessary, the associated pin clamping nut 48 is tightened, using a wrench (not shown) to engage the head 52 of the clamping nut 48. This tightening motion causes the associated flexible sleeve 50 to be compressed along its longitudinal axis, and to expand simultaneously outward, tightly engaging the internally threaded portion 46 of the pin mounting hole 18, and inward tightly engaging the shank 42 of the pin 32. In this way, the pin 32 is tightly clamped in place within the fixation device 10.

The flexible sleeves 50 are preferably composed of an elastomer, (i.e. of a polymeric material having elastic properties of a natural rubber), since such a material is particularly effective in converting compression in a first direction into expansion in directions perpendicular to the first direction.

Figure 3:
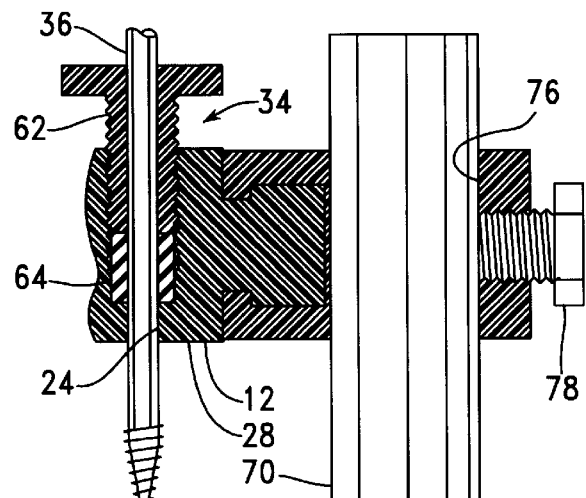
FIG. 3 is a second transverse cross-sectional view, taken as indicated by section lines III—III in FIG. 1 to show a second pin clamping mechanism and a attachment block within the fixation device of FIG. 1.

FIG. 3 is a transverse cross-sectional view, taken through the widened section 28 of plate 12 and through the attachment block 14 as indicated by section lines III—III in FIG. 1.

Referring to FIGS. 1 and 3, the pin mounting holes 24 in the second pin mounting pattern 26 include a number of pin clamping mechanisms 34 holding pins 36. In particular, these pins 36 are driven into one or more bone fragments separated from the remaining portion of the radius 56 by a distal fracture indicated by a phantom line 60. (While there is no indication, in the typical application shown in FIG. 1, that a pin clamping mechanism 34 should be installed within the particular pin mounting hole 24 through which section lines III—III extend, such a mechanism 34 is shown in this hole for purposes of simplifying the illustrations.) The pin 36 and the second pin clamping mechanism 34 are similar, in construction and in the process of installation, to the pin 32 and the first pin clamping mechanism 30, which have been described above in reference to FIG. 2, except that the various diameters of the pin 36 and the second pin clamping mechanism 34 are smaller to provide for closer placement of the pins 36. Thus, the second pin clamping mechanism 34 includes a pin clamping nut 62 and an flexible sleeve 64. The pin mounting holes 24 are preferably arranged in a close-packed array as shown, with rows of holes 24 being staggered to maximize the number of holes 24 which are presented over the distal end of the radius. In this way, pins 36 are provided for attachment to several fragments broken away in a comminuted fracture.

Figure 4:
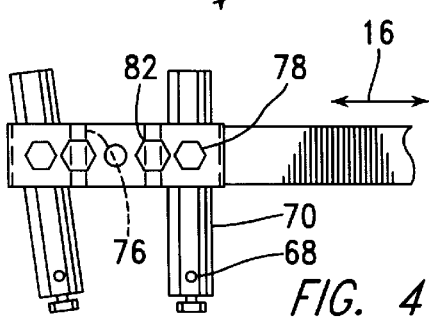
FIG. 4 is a fragmentary front elevation of the fixation device of FIG. 1.

FIG. 4 is a fragmentary front elevation of the fixation device 10, showing particularly the attachment block 14.

Referring to FIGS. 1, 3, and 4, the attachment block 14 is used to provide support for one or more pins 68 extending laterally into bone or bone fragments. Each pin 68 is held at a lower end of a cylindrical bar 70 by means of a pin clamping screw 72. With the clamping screw 72 loosened, lateral movement of the pin 68, in the directions of arrow 74, is permitted. Such movement is required during the process of installing the pin 68 into bone. The cylindrical bar 70 is in turn clamped within an elongated hole 76 in the attachment block 14 by means of a clamping screw 78. The attachment block 14 moves longitudinally, in the directions of arrow 16, being slideably mounted on the plate 12 by means of a track 80, and being clamped in place by a pair of clamping screws 82. Further adjustment of the individual pins 68 is provided by the elongation of holes 76, which allows the angular adjustment of the cylindrical bars 70, as shown in FIG. 4.

Various components of the fixation device 10 are preferably composed of materials which are radiotransparent, so that X-rays can be used to determine the configuration of bone segments during the installation of the fixation device 10 and during the subsequent healing process. Such components include the plate 12, the attachment block 14, the rods 70, and the clamping nuts 48, 62. These components are composed, for example of polycarbonate. Carbon filament composites may also be used. The pins 32, 36, 68, which are inserted into the human body, are preferably stainless steel.

While the exemplary device shown in FIG. 1 is configured particularly for use in the repair of a distal radius fracture of the right arm, it is apparent that similar device, having a different plate 12, but other components as described above, and remaining within the scope of the present invention, could be configured for the repair of a distal radius fracture of the left arm. It is also apparent that a similar device, extending to provide similar probe position holes 24 and a track for the attachment block 14 on either side, and remaining within the scope of the present invention, can be configured for the repair of a distal radius fracture of either arm.

While the present invention has been described in terms of a device for the external fixation of a fractured radius, it is understood that the method of the present invention can be used for clamping an individual pin in place within another type of fixture for external fixation.

While the present invention has been described in a preferred form or embodiment with some degree of particularly, it is understood that this description has been given only by way of example, and that numerous changes in the details of fabrication and use, including the combination and rearrangement of parts, may be made without departing from the spirit and scope of the invention.

What is claimed is:

1. Apparatus for clamping an external fixation pin within a fixation device, wherein said pin extends inwardly from said fixation device for attachment within bone and outwardly for attachment to a rotary driving device, and wherein said apparatus comprises:
    a pilot hole within said fixation device through which said pin extends;
    an internally threaded hole within said fixation device, in alignment with said pilot hole and larger in diameter than said pilot hole;
    a flexible sleeve within said internally threaded hole, wherein said flexible sleeve includes a hole through which said pin extends;
    a clamping nut including an externally threaded section engaging said internally threaded hole and a hole through which said pin extends, wherein turning said clamping nut to move said clamping nut inward compresses said flexible sleeve in a direction parallel to a longitudinal axis of said flexible sleeve, so that said flexible sleeve expands transversely to clamp said pin and to clamp against said internally threaded hole.

2. The apparatus of claim 1, wherein said flexible sleeve is composed of an elastomer.

3. The apparatus of claim 1, wherein
    said internally threaded hole is outwardly exposed in said fixation device for insertion of said clamping nut therein, and
    said clamping nut additionally includes a hexagonally shaped head extending outward from said fixation device for turning said clamping nut.

4. Apparatus for external bone fixation, comprising:
    a plate;
    a plurality of pin mounting holes extending within said plate, wherein each pin mounting hole within said plurality of pin mounting holes includes an internally threaded portion and a pilot hole aligned with said internally threaded portion;
    a plurality of pins individually extending within various pin mounting holes within said plurality of pin mounting holes, wherein each pin within said plurality of pins extends in a first direction from said plate for attachment within bone and opposite said first direction for attachment to a rotary driving device;
    a plurality of flexible sleeves, wherein each flexible sleeve within said plurality thereof extends over a pin within said plurality of pins and within a pin mounting hole in said plurality of pin mounting holes; and
    a plurality of clamping nuts, wherein each clamping nut within said plurality of clamping nuts includes a central hole and an externally threaded section, wherein each clamping nut within said plurality of clamping nuts extends over a pin within said plurality of pins and into said pin mounting hole through which said pin extends to engage said internally threaded portion of said pin mounting hole, and to compress said flexible sleeve, extending over said pin, along a longitudinal axis of said flexible sleeve, and wherein compressing said flexible sleeve along said longitudinal axis causes said flexible sleeve to expand transversely, clamping said sleeve on said pin and clamping said sleeve within said pin mounting hole.

5. The apparatus of claim 4, wherein each flexible sleeve within said plurality of flexible sleeves is composed of an elastomer.

6. The apparatus of claim 4, wherein said plurality of pin mounting holes includes:
    a first plurality of pin mounting holes extending in a line for attachment of a first plurality of pins extending into a shaft of a fractured bone; and
    a second plurality of pin mounting holes in a two-dimensional array for attachment of pins extending into a fragment of said fractured bone.

7. The apparatus of claim 6, wherein
    said pin mounting holes in said second plurality of pin mounting holes are smaller in diameter than said pin mounting holes in said first plurality of pin mounting holes, and
    said pins extending within said second plurality of pin mounting holes are smaller in diameter than said pins extending within said first plurality of pin mounting holes.

8. The apparatus of claim 6, additionally including:
    an attachment block, slidably mounted on said plate adjacent said first plurality of pin attachment holes, wherein said attachment block includes a plurality of rod attachment holes;
    a rod, extending within a rod mounting hole within said plurality of rod mounting holes, and extending from said attachment block in said first direction; and
    a pin extending within said rod and extending in a lateral direction toward said first plurality of pins.

9. The apparatus of claim 8, wherein said rod extends loosely within said rod mounting hole to be within said rod mounting hole at an adjustable angle.

10. The apparatus of claim 4, additionally including:
    an attachment block, slidably mounted on said plate to move along an edge of said plate and to be clamped in place on said plate, w herein said attachment block includes a plurality of rod attachment holes;
    a rod, extending within a rod mounting hole within said plurality of rod mounting holes, and extending from said attachment block in said firs t direction; and
    a pin extending within said rod and extending in a lateral direction perpendicular to said first direction.

11. The apparatus of claim 10, wherein said rod extends loosely within said rod mounting hole to be clamped within said rod mounting hole at an adjustable angle.

12. The apparatus of claim 11, wherein said rod is composed of a radiotransparent material.

13. The apparatus of claim 12, wherein said plate, each of said flexible sleeves within said plurality of flexible sleeves, and each clamping nut within said plurality of clamping nuts are composed of radiotransparent materials.

14. The apparatus of claim 4, wherein said plate, each of said flexible sleeves within said plurality of flexible sleeves, and each clamping nut within said plurality of clamping nuts are composed of radiotransparent materials.

15. Apparatus for external fixation of a fractured distal radius, wherein said apparatus comprises:
   a plate;
   a first plurality of pin mounting holes extending in a line within said plate for securing pins in a shaft portion of said fractured distal radius;
   a second plurality of pin mounting holes extending in a two-dimensional array within said plate for securing pins in a fragment of said fractured distal radius;
   a first plurality if pins individually extending within various of said pin mounting holes within said first plurality of pin mounting holes, wherein each of said pins in said first plurality of pins extends in a first direction from said plate for attachment within bone;
   a second plurality of pins individually extending within various of said pin mounting holes within said second plurality of pin mounting holes, wherein each of said pins in said second plurality of pins extends in said first direction from said plate for attachment within bone;
   an attachment block slidably mounted to said plate adjacent said first plurality of pin mounting holes, wherein said attachment block includes a plurality of rod mounting holes;
   a rod, extending within a rod mounting hole within said plurality of rod mounting holes, and extending from said attachment block in said first direction; and
   a pin extending within said rod and extending in a lateral direction toward said first plurality of pins.

16. The apparatus of claim 15, wherein said rod extends loosely within said rod mounting hole to be within said rod mounting hole at an adjustable angle.

17. Apparatus for external fixation of a fractured distal radius, wherein said apparatus comprises:
   a plate;
   a first plurality of pin mounting holes extending in a line within said plate for securing pins in a shaft portion of said fractured distal radius;
   a second plurality of pin mounting holes extending in a two-dimensional array within said plate for securing pins in a fragment of said fractured distal radius, wherein each pin mounting hole within said first and second pluralities of pin mounting holes includes a pilot hole and an internally threaded hole;
   a first plurality if pins individually extending within various of said pin mounting holes within said first plurality of pin mounting holes, wherein each of said pins in said first plurality of pins extends in a first direction from said plate for attachment within bone;
   a second plurality of pins individually extending within various of said pin mounting holes within said second plurality of pin mounting holes, wherein each of said pins in said second plurality of pins extends in said first direction from said plate for attachment within bone;
   a flexible sleeve extending around each pin in said first and second pluralities of pins; and
   a clamping nut extending around each pin in said first and second pluralities of pins, wherein each said clamping nut engages said internally threaded hole within said pin mounting hole through which said pin extends, and turning said clamping nut to move said clamping nut in said first direction causes said clamping nut to compress said flexible sleeve in a direction parallel to a longitudinal axis of said flexible sleeve, so that said flexible sleeve expands transversely to clamp said pin and to clamp against said internally threaded hole.

18. The apparatus of claim 17, wherein each said flexible sleeve is composed of an elastomer.

19. The apparatus of claim 17, wherein
   each pin in said second plurality of pins is smaller in diameter than each pin in said first plurality of pins,
   said sleeve extending around each pin in said second plurality of pins is smaller in diameter than said sleeve extending around each pin in said first plurality of pins, and
   said clamping nut extending around each pin in said second plurality of pins is smaller in diameter than said clamping nut extending around each pin in said first plurality of pins.

20. The apparatus of claim 17, wherein said plate, each of said flexible sleeves, and each of said clamping nuts are composed of radiotransparent materials.

* * * * *